US012595453B2

(12) United States Patent　(10) Patent No.:　US 12,595,453 B2
　Gustafsson et al.　(45) Date of Patent:　Apr. 7, 2026

(54) DEVICE FOR SUPPLYING AND DISCHARGING A MEDIUM; CULTURE VESSEL HAVING SUCH A DEVICE AND METHOD OF CULTIVATING MICROBIOLOGICAL SYSTEMS BY USING SUCH A CULTURE VESSEL

(71) Applicant: Naturin Viscofan GmbH, Weinheim (DE)

(72) Inventors: Leon Gustafsson, Tuebingen (DE); Martin Vaegler, Berlin (DE); Karl-Dietrich Sievert, Bodman-Ludwigshafen (DE)

(73) Assignee: Naturin Viscofan GmbH, Weinheim (DE)

( * ) Notice: Subject to any disclaimer, the term of this patent is extended or adjusted under 35 U.S.C. 154(b) by 1032 days.

(21) Appl. No.: 17/196,034

(22) Filed: Mar. 9, 2021

(65) Prior Publication Data

US 2021/0189316 A1　Jun. 24, 2021

Related U.S. Application Data

(63) Continuation of application No. PCT/EP2019/073866, filed on Sep. 6, 2019.

(30) Foreign Application Priority Data

Sep. 17, 2018　(DE) ..................... 10 2018 122 745.0

(51) Int. Cl.
　*C12M 1/00*　(2006.01)
　*C12M 1/24*　(2006.01)
(52) U.S. Cl.
　CPC ............ *C12M 29/06* (2013.01); *C12M 23/08* (2013.01); *C12M 23/38* (2013.01)

(58) Field of Classification Search
　CPC ............................. C12M 23/08; C12M 23/40
　See application file for complete search history.

(56) References Cited

U.S. PATENT DOCUMENTS 4,087,327　A　*　5/1978　Feder ..................... C12M 23/04
　　　　　　　　　　　　　　　　　　　　　　435/399
4,699,884　A　　10/1987　Noss et al.
　　　　　　　　　(Continued)

FOREIGN PATENT DOCUMENTS

DE　　　10201259　A1　　8/2003
EP　　　0589632　A1　　3/1994
　　　　　　(Continued)

OTHER PUBLICATIONS

International Preliminary Report on Patentability for International Application No. PCT/EP2019/073866, mailed Mar. 25, 2021.
(Continued)

*Primary Examiner* — Michael A Marcheschi
*Assistant Examiner* — Nathan G Esperon
(74) *Attorney, Agent, or Firm* — Jason H. Vick; Amped IP LLC

(57)　　　　　　　　ABSTRACT

A device for the supply or discharge of medium into or out of a culture vessel comprises a housing on which a first aperture and a plurality of second apertures are arranged. The first aperture and the second apertures have fluid-conducting connection to one another in a manner to supply a medium from the first aperture via the second apertures into the interior of the culture vessel or to discharge same in reversed direction therefrom, when the device is attached on the culture vessel. The plurality of second apertures are configured to generate a plurality of medium sub-streams arranged in parallel to one another of the medium that is to (Continued)

be supplied or that is to be discharged. Further disclosed are a culture vessel and a method of cultivating microbiological systems.

6 Claims, 7 Drawing Sheets

(56) References Cited

U.S. PATENT DOCUMENTS

| | | | | |
|---|---|---|---|---|
| 4,839,292 | A * | 6/1989 | Cremonese | C12M 23/34 |
| | | | | 435/297.2 |
| 5,240,854 | A * | 8/1993 | Berry | C12M 23/04 |
| | | | | 435/305.1 |
| 9,677,038 | B2 * | 6/2017 | Stobbe | C12M 23/44 |
| 2002/0039785 | A1 | 4/2002 | Schroeder et al. | |
| 2005/0084954 | A1 | 4/2005 | Bader | |
| 2009/0191620 | A1 * | 7/2009 | Martin | C12M 23/40 |
| | | | | 435/294.1 |
| 2014/0120608 | A1 * | 5/2014 | Carter | C12M 23/40 |
| | | | | 435/289.1 |
| 2014/0186941 | A1 * | 7/2014 | Zhou | C12M 47/04 |
| | | | | 435/289.1 |
| 2016/0186113 | A1 * | 6/2016 | Tanner | C12M 23/34 |
| | | | | 435/297.1 |

FOREIGN PATENT DOCUMENTS

| | | | | |
|---|---|---|---|---|
| WO | WO 2006/130670 | | 12/2006 | |
| WO | WO-2016069892 | A1 * | 5/2016 | C12M 1/268 |

OTHER PUBLICATIONS

International Search Report for International Application No. PCT/EP2019/073866, mailed Dec. 3, 2019.
Written Opinion for International Application No. PCT/EP2019/073866, mailed Dec. 3, 2019.

* cited by examiner

DEVICE FOR SUPPLYING AND DISCHARGING A MEDIUM; CULTURE VESSEL HAVING SUCH A DEVICE AND METHOD OF CULTIVATING MICROBIOLOGICAL SYSTEMS BY USING SUCH A CULTURE VESSEL

CROSS-REFERENCE TO RELATED APPLICATIONS

This application is a continuation of international patent application PCT/EP2019/073866, filed on Sep. 6, 2019 designating the U.S., which international patent application claims priority from German patent application 10 2018 122 745.0, filed on Sep. 17, 2018. The entire contents of these priority applications are incorporated herein by reference.

FIELD OF THE INVENTION

The present invention relates to a device for supplying or discharging a medium into or out of a culture vessel. The invention further relates to a culture vessel comprising such a device, and to a method of cultivating microbiological systems, in particular cell cultures, using such a culture vessel.

BACKGROUND

A device of the type mentioned above is used for growing or cultivating microbiological systems, in particular cells or microorganisms, in a culture vessel, for example in a bioreactor.

It is thus possible to keep alive microbiological systems, such as cells, tissue and/or microorganisms, outside of an organism, in order to permit study of their development in greater detail. During the cultivating of cells (cell culture) and during what is known as "tissue engineering" it is necessary to provide, to the cells located in the culture vessel, in particular adherent cells or cells in suspension, a medium that comprises the substances needed for the development of the cells, for example nutrients or oxygen.

A device of the type mentioned at the outset serves for the supply of the medium; this medium, which by way of example is taken from a medium reservoir, is introduced through a first aperture into the housing of the device attached on the culture vessel. In this case, the device serves as supply device. Since the first aperture has fluid-conducting connection to a second aperture, the incoming medium can reach the second aperture and emerge through same. Finally, the emerging medium reaches the interior of the culture vessel, and can be received by the cells located there.

The device mentioned above can also serve as discharge device for the discharge of the medium, in particular of the used-up nutrient medium, from the culture vessel. In this case, the nutrient medium is removed by suction from the interior of the culture vessel through the second aperture into the housing of the discharge device attached on the culture vessel, and the nutrient medium is thus discharged from the housing by way of the first aperture. The used-up medium can thus be removed from the culture vessel.

The principle of operation described above for supply and discharge of a medium is known by way of example from DE 102 01 259 A1. Provided in the device disclosed there are an inlet connection bore and a return connection bore, intended for introduction of nutrient medium and optionally also oxygen into the cell culture space within the container by way of appropriate conduit connections or flexible-tube connections.

However, the known device has the disadvantage of only limited controllability of the flow of the nutrient medium or of the oxygen in the cell culture space. Thereby, the nutrient medium entering through the inlet connection bore into the cell culture space cannot be conducted at a defined flow rate in the direction of the return connection bore. Large variations of the quantity of nutrients or oxygen present in the cell culture space therefore occur, so that the cells to be cultivated can be subject to temporal and/or spatial over- or undersupply; this, however, can adversely affect cell development.

SUMMARY

It is an object of the present invention to provide a device of the type mentioned in the introduction with the aim of permitting better control of the flow of the medium in the interior of the culture vessel, in order to reduce, or entirely avoid, variations of the quantity of the medium present in the culture vessel.

According to an aspect of the invention, a device configured to supply or discharge a medium into or out of a culture vessel is provided, comprising a housing, a first aperture and a plurality of second apertures arranged on the housing, the plurality of second apertures being connected with the first aperture in fluid-conducting manner to supply a medium from the first aperture via the second apertures into an interior of the culture vessel or to discharge a medium from the interior of the culture vessel in reversed direction, when the device is attached on the culture vessel, such that a plurality of medium sub-streams, arranged in parallel to one another, of the medium to be supplied or to be discharged are generated.

Because each of the plurality of second apertures is connected in fluid-conducting manner with the first aperture, the medium entering through the first aperture into the housing of the device, in particular of the supply device, can reach each of the plurality of second apertures. The incoming medium can in turn emerge through these and finally reach the interior of the culture vessel. A plurality of medium strings or medium sub-streams are thus produced from the incoming medium stream, these being arranged in parallel to one another. An incoming stream is thus advantageously distributed into a plurality of outgoing streams, thus achieving particularly uniform distribution of the overall flow of the medium in the interior of the culture vessel.

The arrangement of the plurality of second apertures is moreover particularly advantageous for reducing, or entirely avoiding, swirling effects. Because of a plurality of medium sub-streams arranged in parallel to one another are generated, mixing of different medium sub-streams is greatly reduced, and this has a favorable effect on minimization of swirling or turbulence effects in the flow of the medium. The flow behavior of the medium in the interior of the culture vessel can thus be better controlled.

The abovementioned advantages also apply to the case in which the device serves as discharging device for discharging the used-up medium by way of the plurality of second apertures into the housing of the device and finally outward (for example into a return conduit). Here again, the arrangement of the plurality of second apertures promotes a uniform flow distribution of the medium in the interior of the culture vessel. Here again, turbulence effects in the medium stream are moreover reduced or entirely avoided.

The particular advantage for cell development, alongside the reduced variation of the quantity of ingredients in the interior of the culture vessel, is minimization of swirling or turbulence effects, and in particular laminar flow of the medium. If swirling effects are present, the cells located in the culture vessel, in particular adherent cell lawns, fixed cell assemblages, or biopsy samples and tissue samples, can be subjected to a swirling motion that can damage, or entirely destroy, the interior structure of the cells. This risk is advantageously reduced by the provision of the plurality of medium sub-streams, arranged in parallel to one another, of the medium that is to be introduced or to be discharged.

Increased laminarity of flow of the medium moreover permits achievement of an almost constant flow rate, thus permitting mechanical stimulation of the adherent cells or cell lawns and/or tissue during growth of the cells. Growth conditions provided during cell development and cell differentiation can thus simulate natural conditions.

Continuous and dynamic cultivation of cells and tissues under controllable, in particular laminar, flow conditions is advantageously permitted. The present invention is therefore particularly suitable for the cultivation of adherent urothelium cells intended to expand in multiple layers. The present invention can moreover also be used for short-, medium- and/or long-term studies of other adherent cell types.

In a preferred embodiment, the first aperture is connected with each of the plurality of second apertures respectively via one of a plurality of fluid conduits arranged in parallel to one another.

The medium stream entering into the first aperture is thus, upstream of the plurality of second apertures, already divided into a plurality of sub-streams. This facilitates the generation of the plurality of medium sub-streams of the medium that is to be introduced or that is to be discharged, and this promotes reduction of swirling effects in the interior of the culture vessel.

In another preferred embodiment, at least one of the plurality of fluid conduits is configured at least partially as nozzle, in particular as laminar nozzle for generating a laminar medium sub-stream of the plurality of medium sub-streams.

A nozzle is a flow duct with a cross section that changes in flow direction, and has the advantage that medium supply and medium discharge take place with no, or only with slight, loss of flow velocity. The nozzle advantageously promotes a defined flow rate of the medium in the interior of the culture vessel.

The nozzle preferably comprises a laminar nozzle for generating a laminar medium sub-stream. It is thus easily and advantageously possible to generate at least one of the plurality of medium sub-streams as laminar medium sub-stream. The laminar nozzle can have a tube diameter that, for flow velocities of the medium that are appropriate for the development of the cells, gives a Reynolds number that is below 2300, preferably below 2000.

In another preferred embodiment, the nozzle has an external and/or internal cross section which at least sectionally narrows in the direction of the second aperture associated with said nozzle.

This type of nozzle is particularly advantageous for achieving a particularly uniform flow rate. The controllability of the medium flow is thus further improved.

In another preferred embodiment, at least one of the plurality of fluid conduits has a tubular terminal section which is curved toward the second aperture associated with the at least one fluid conduit.

The curvature results in an advantageously uniform change of the flow direction of the medium before exit from the second aperture and/or before entry into the second aperture, for example from a direction perpendicular to the bottom of the culture vessel to a direction parallel to the bottom. It is thus possible to mitigate, or entirely avoid, any abrupt change of direction of the medium stream, thus further reducing swirling effects.

In another preferred embodiment, at least one of the plurality of fluid conduits is directed at least sectionally perpendicularly to a bottom side of a vessel body of the culture vessel.

This has the advantage that the force exerted by the intrinsic weight of the medium can be utilized for the supply of medium when the device is arranged on the culture vessel, where the bottom side of the vessel body is oriented horizontally. The power needed for the pump for introducing the medium into the device is thus advantageously reduced.

In another preferred embodiment, a shared intermediate chamber is configured in the housing for the fluid-conducting connection between the first aperture on the one hand and the plurality of fluid conduits on the other hand.

The shared intermediate chamber is connected not only to the first aperture but also to the plurality of second apertures via the plurality of fluid conduits. The shared intermediate chamber advantageously permits a particularly uniform flow transition between the first aperture and each of the plurality of second apertures.

In another preferred embodiment, the first aperture is arranged centrally on a surface of the housing and/or is arranged terminally on a tube section projecting beyond the surface of the housing.

The first aperture thus arranged promotes a uniform distribution of the medium that is to be introduced and/or that is to be discharged. The tube section projecting beyond the surface of the housing permits easy connection for flexible tubes which by way of example are connected to a medium reservoir and/or a pump for the supply or discharge of medium.

In another preferred embodiment, the housing comprises a base body and a cover for the releasable closure of the base body.

In this embodiment, the device of the invention is configured in two parts. Easier handling of the device of the invention is thus achieved, alongside greater ease of replacement of the cover and of the base body.

According to another aspect of the invention, a culture vessel, in particular a bioreactor for the cultivation of microbiological systems, for example of cells and/or microorganisms, is provided, comprising a vessel body configured to accommodate a medium and extending from an upper side to a bottom side, and at least one device configured to supply or discharge a medium into or out of the vessel body and arranged on an upper side of the vessel body, the at least one device comprising: a housing, a first aperture and a plurality of second apertures arranged on the housing, the plurality of second apertures being connected with the first aperture in fluid-conducting manner to supply a medium from the first aperture via the second apertures into an interior of the vessel body or to discharge a medium from the interior of the vessel body in reversed direction, such that a plurality of medium sub-streams, arranged in parallel to one another, of the medium to be supplied or to be discharged are generated.

The culture vessel, in particular the bioreactor vessel, is preferably treated by a sterilization method conventionally used in tissue engineering, so that it can be used in good manufacturing practice (GMP) production processes.

In a preferred embodiment, at least one plug-in aperture arranged to plug-in the at least one device is arranged on the upper side of the vessel body.

This permits accommodation of the device on the vessel body of the culture vessel in a manner that is secure and particularly easy to implement.

In another preferred embodiment, the at least one device comprises, on the vessel body, a first device for the supply of the medium, and a second device for the discharge of the medium.

With this measure, it is possible to utilize the abovementioned advantages of the device of the invention not only for supplying the medium but also for discharging the medium. The controllability of the flow rate in the culture vessel is advantageously further increased.

Preferably, the first and the second devices are arranged at two mutually opposite edges of the vessel body.

This can provide particularly uniform flow of the medium between the two edges of the vessel body. This advantageously promotes cell development of the adherent cells in the entire region between the edges of the vessel body.

In another preferred embodiment, the plurality of second apertures are respectively arranged with an adjustable distance from the bottom side of the vessel body.

It is thus advantageously possible to avoid damage to the device caused by impacts involving the bottom side of the vessel body. It is moreover possible to achieve particularly precise control of the flow behavior of the medium in the vessel body by adjusting the distance of the second apertures from the bottom side.

In another preferred embodiment, the vessel body comprises a connection for electrical current and/or voltage arranged for the application of an electrical current and/or an electrical voltage on the vessel body.

With this measure it is possible to establish an internal membrane potential of the individual cells located in the vessel body, in order to promote growth and cell proliferation. The typical electrical voltage to be applied on the culture vessel, in particular bioreactor vessel, is by way of example in the range of about 0 mV to 100 mV.

According to another aspect of the invention, a method of cultivating microbiological systems, for example cells and/or microorganisms, comprises using a culture vessel according to one of the above embodiments.

Further advantages and features will be apparent from the description below and from the attached drawing.

It is self-evident that the abovementioned features and the features that will be explained below can be used not only in the respective stated combination but also in other combinations, or alone, without leaving the scope of the present invention.

BRIEF DESCRIPTION OF THE DRAWINGS

Exemplary embodiments of the invention are shown in the drawings, and are described hereinbelow with reference to said drawings, in which.

EMBODIMENTS

Figure 1:
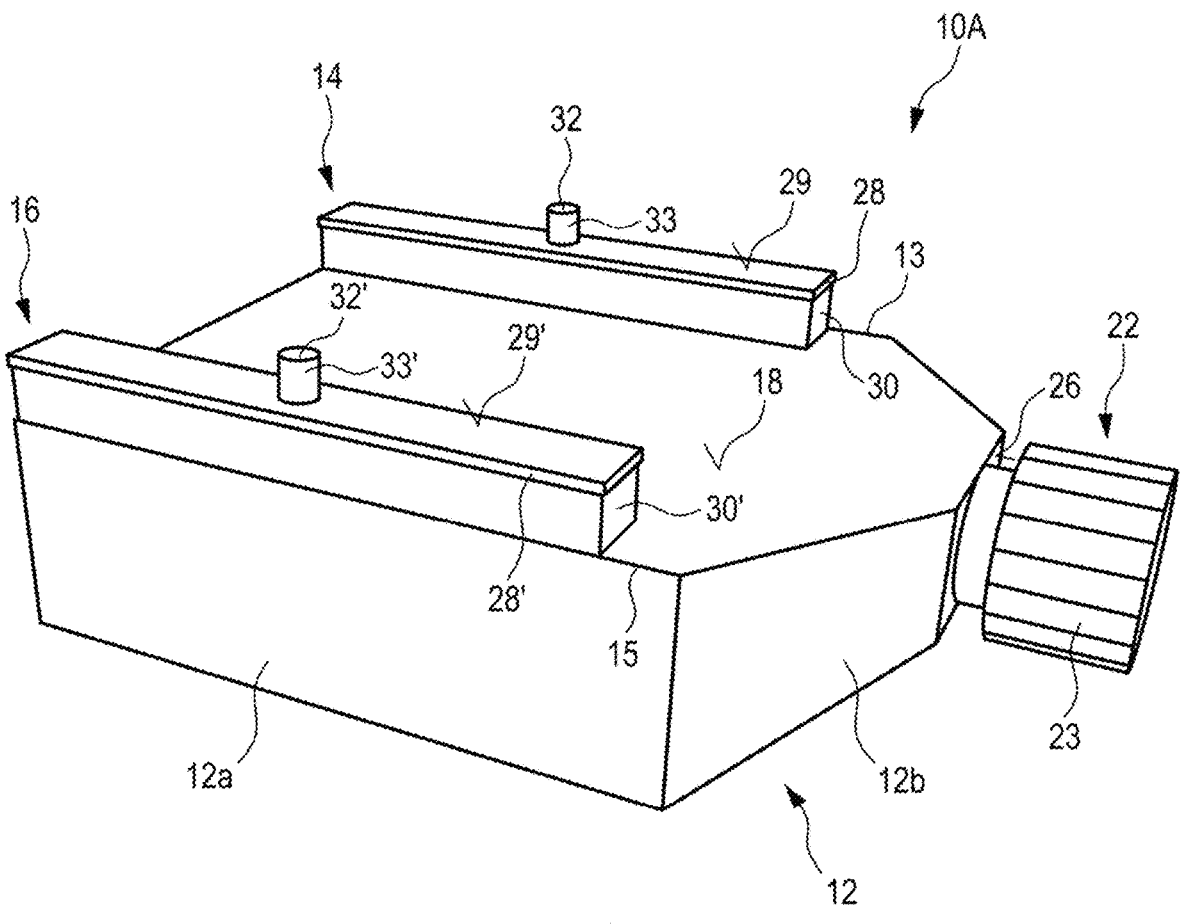
FIG. 1 shows a perspective view of a bioreactor for cultivating microbiological systems, comprising devices for the supply and discharge of medium.

FIG. 1 shows a bioreactor 10A for the cultivation of microbiological systems, for example of cells and/or microorganisms. The bioreactor 10A comprises a vessel body 12 to receive a medium, for example a nutrient medium, and/or a gas such as oxygen. The bioreactor 10A moreover comprises a first device 14 for the supply of medium into the vessel body 12, and a second device 16 for the discharge of medium from the vessel body 12. The vessel body 12 extends from upper side 18 to a bottom side 20 not shown here (see FIG. 2), there being, arranged between the upper side 18 and the bottom side 20, an internal space 19 (see FIG. 2) of the vessel body 12. The vessel body 12 moreover comprises a lateral face 26, on which a vessel neck 22 which can be closed by a cap 23 is arranged.

As can be seen from FIG. 1, the vessel body 12 comprises a first section 12a which has the shape of a rectangular parallelepiped and in which the upper side 18 runs in essence parallel to the bottom side 20, and a second section 12b which has the shape of a trapezoid and in which, at the side having the vessel neck, the upper side 18 is inclined in the direction of the bottom side 20. The first and the second device 14, 16 are attached at two mutually opposite edges 13, 15 of the first section 12a having the shape of a rectangular parallelepiped.

The first device 14 comprises a base body 30 and a cover 28 for releasable closure of the main body 30. Arranged centrally on a surface 29 of the cover 28 is a first aperture 32, arranged at the end of a tube section 32 projecting beyond the surface 29 of the cover 28. The cover 28 and the base body 30 form a housing of the first device 14.

The second device 16 is similar to the first device 14 in likewise comprising a cover 28' for releasable closure of a base body 30', wherein, centrally arranged on a surface 29' of the cover 28', is a tube section 33' which has, at its end, a first aperture 32' of the second device 16.

Flexible tubes for the feed or return of a medium, for example a nutrient medium comprising a plurality of ingredients, or a gas such as oxygen, can be attached to the first aperture 32, 32', and the flexible tubes can be attached to a pump and/or a medium reservoir.

Figure 2:
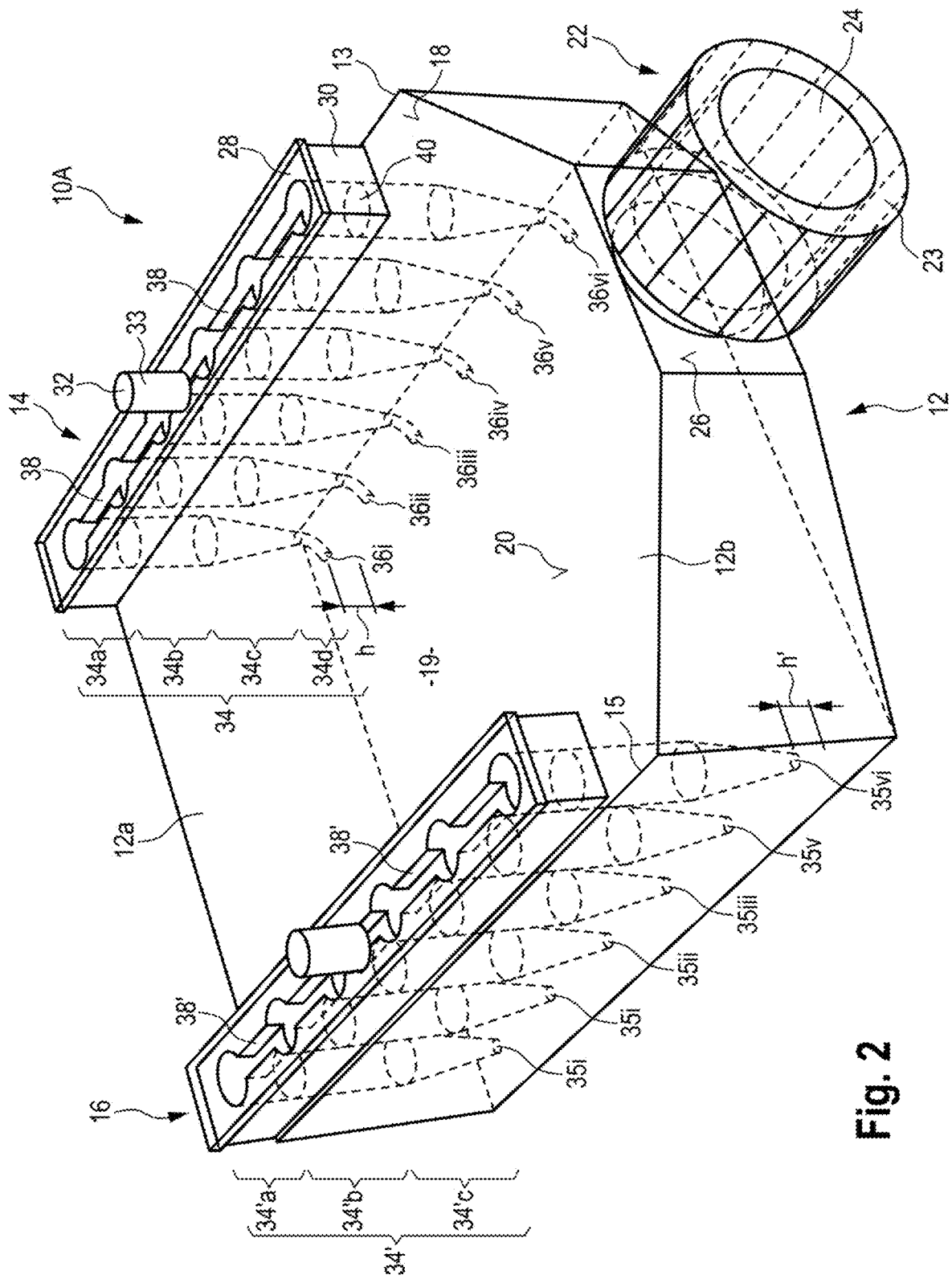
FIG. 2 shows another perspective view of the bioreactor from FIG. 1.

FIG. 2 shows another perspective view of the bioreactor 10A from FIG. 1, wherein the first and second devices 14, 16 are shown in more detail. For illustrative purposes, the vessel body 12 and the first and second devices 14, 16 are shown in transparent view.

The first device 14 is by way of example a supply device, and comprises a plurality of nozzles 34 which are connected in fluid-conducting manner with the tube section 33 via a shared intermediate chamber 38 extending in a longitudinal direction of the first device 14. The nozzles 34 extend from the shared intermediate chamber 38 perpendicularly to the upper side 18 of the rectangular parallelepiped-shaped first section 12*a* in the direction of the bottom side 20, and respectively terminate in a second aperture 36*i-vi*. The plurality of nozzles 34 here are respectively inserted into the internal space 19 of the vessel body 12 via a plug-in aperture 40, these being arranged on the upper side 18 of the vessel body 12.

The plurality of nozzles 34 are distributed over the entire length of the shared intermediate chamber 38, and arranged at a distance from one another. Each nozzle 34 comprises a plurality of successive nozzle sections 34*a, b, c, d*. A first nozzle section 34*a*, which is configured as cylinder, extends within the base body 30 of the first device 14, preferably from the shared intermediate chamber 38 to the level corresponding to the associated plug-in aperture 40 of the vessel body 12. The first nozzle section 34*a* can be fixed on the cover 28. Alternatively, the first nozzle section 34*a* of the nozzle 34 can be arranged as a bore within, and running through, the vessel body 30.

A second nozzle section 34*b*, which is likewise configured as cylinder, extends from the first nozzle section 34*a* in the direction of the bottom side 20 of the vessel body 12. As can be seen in FIG. 2, the two sections 34*a, b* have the same internal diameter. The second section 34*b* is preferably arranged as longitudinal extension of the first section 34*a* fixed on the cover 28. Alternatively, the second nozzle section 34*b* can be fixed on the base body 30.

A third nozzle section 34*c* extends from the second nozzle section 34*b* in the direction of the bottom side 20 of the vessel body 12. As can be seen in FIG. 2, the third nozzle section 34*c* has a conical shape, where the external cross section and the internal cross section of the conical shape narrows in the direction toward the bottom side 20.

The plurality of nozzles 34 provide a fluid conduit between the first aperture 32 and each of the second apertures 36*i-iv*. The nozzles 34 arranged in parallel to one another advantageously produce a plurality of medium substreams (medium strings) of the incoming medium, arranged in parallel to one another. The fluid conduits are moreover distributed over the length of the first device 14, and therefore also over the length of the edge 13, and the incoming medium stream is therefore particularly uniformly distributed over the area of the basal side 20. This greatly reduces, or entirely avoids, temporal or spatial over- or undersupply of the cells in the vessel body 12.

The spatial separation of the nozzles 34 moreover greatly reduces, or entirely avoids, disadvantageous mixing of the plurality of medium sub-streams of the medium that is to be introduced. This promotes laminar flow, or flow with little swirling and little turbulence, of the medium in the internal space 29 of the vessel body 12, with defined flow rate, and allows a laminar flow configuration. The flow behavior of the medium is advantageously easier to control, thus providing a further reduction of temporal or spatial over- or undersupply of the cells in the vessel body 12. Cultivation of the microbiological systems located in the vessel body 12, in particular of the adherent cell types/cell lawns and/or microorganisms, is thus further promoted.

Arranged at the end of the respective third nozzle section 34*c* is a tubular fourth nozzle section 34*d*. The fourth nozzle section 34*d* extends from the third nozzle section 34*c* to the second aperture 36*i-vi*, and has a curvature in the direction toward the second aperture 36*i-vi*. The aperture direction of the second aperture 36*i-vi* therefore differs, by an angle that is preferably 90°, from the direction in which the other nozzle sections 34*a, b, c* extend. The curvature prevents sudden change of the flow direction during emergence into the internal space 19, thus further reducing swirling/turbulence effects and further increasing the laminarity of flow of the medium.

At least one of the nozzles 34 can moreover be configured as laminar nozzle suitable for producing a laminar medium sub-stream of the medium that is to be supplied. It is preferable that the laminar nozzle has a Reynolds number that is below 2300, more preferably below 2000, for a flow velocity, and also a viscosity of the medium to be supplied, that is conventional for the cell culture.

The second device 16 is by way of example a discharge device, and likewise comprises a plurality of fluid conduits in the form of nozzles 34', each of which extends between a shared intermediate chamber 38' and a second aperture 35*i-vi*. The only difference from the nozzles 34 of the first device 14 is that the nozzles 34' of the second device 16 respectively have only the first, the second and the third nozzle section 34*a'*, b', c'. As can be seen in FIG. 2, the first and the second device 14, 16 are oriented in relation to one another in a transverse direction. Advantageously, turbulence effects are further reduced, and a defined flow rate of the medium in the internal space 19 is further promoted.

As can be seen in FIG. 2, the second apertures 36*i-vi* of the first device 14 are arranged spaced apart from the bottom side 20 of the vessel body 12. The distance h (measured from the center of the respective second aperture 36*i-iv*) from the bottom side 20 is preferably variable. The second apertures 35*i-iv* of the second device 16 are also arranged with a preferably variable distance h' from the bottom side 20.

Figure 3:
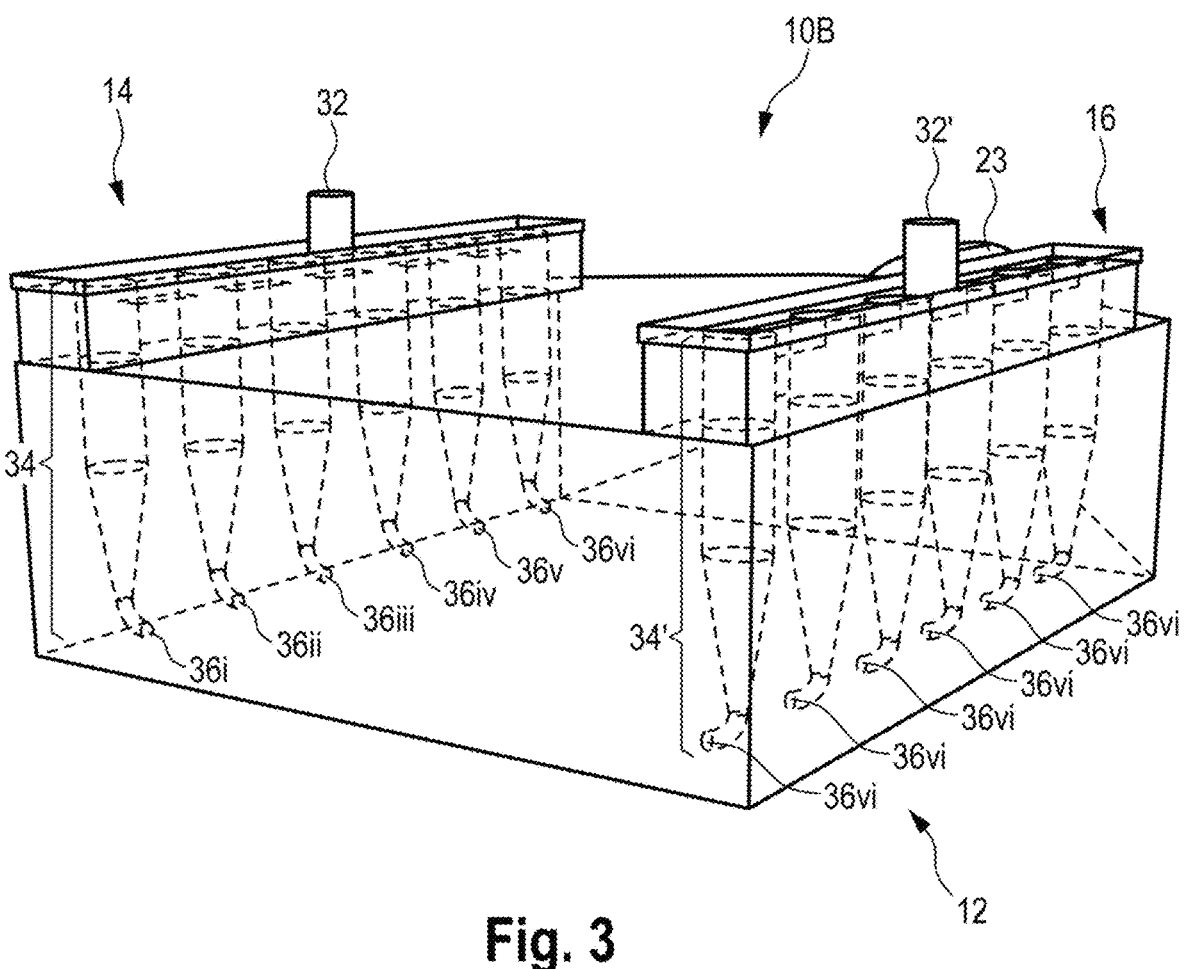
FIG. 3 shows a perspective view of another embodiment of a bioreactor.

FIG. 3 shows a perspective view of another bioreactor 10B with configuration similar to that of the bioreactor 10A from FIGS. 1 to 3, the only difference being that in the case of the bioreactor 10B the first and second device 14, 16 are identical. Each nozzle 34' of the second device 16 therefore comprises, alongside the first, second and third nozzle section 34*a'*, b', c', a tubular fourth nozzle section 34*d'* with a curvature. The second apertures 36*i-iv* of the first device 14 on the one hand and the second apertures 36'*iv* of the second device 16 on the other hand are arranged to face toward one another. Advantageously, swirling/turbulence effects are further reduced, and laminarity of flow of the medium is further increased. Here again, for illustrative purposes, the various components of the bioreactor 10B are shown in transparent view.

Figures 4, 5:
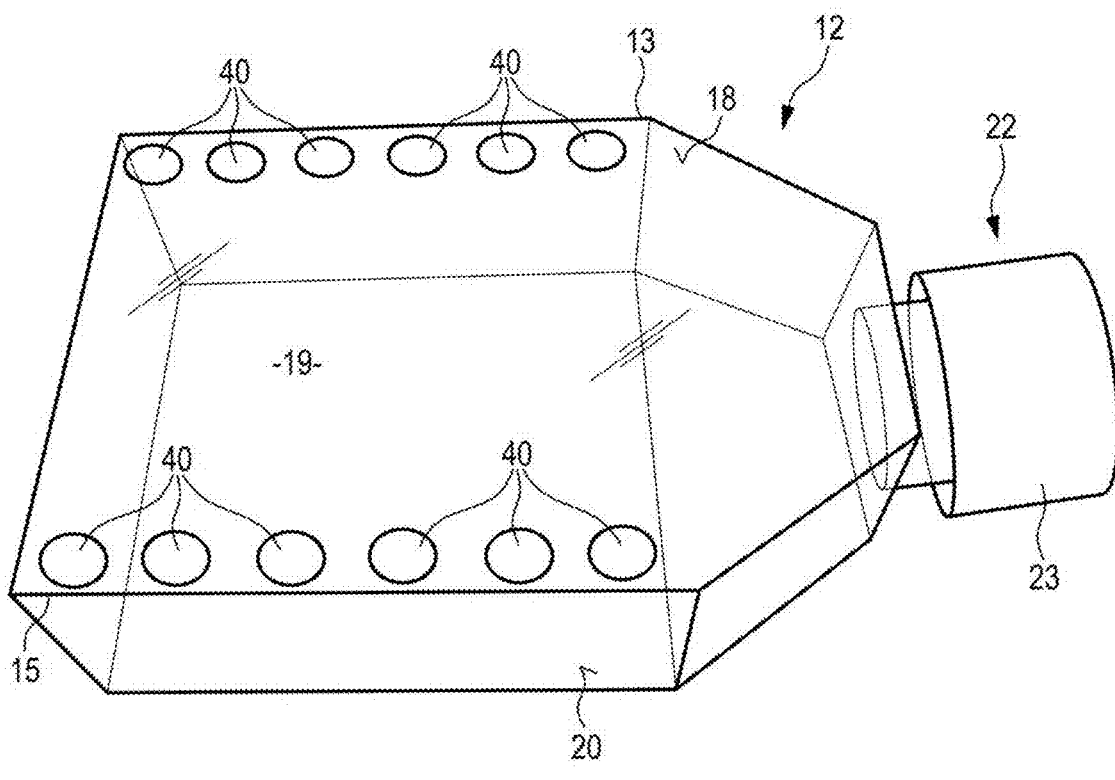
FIG. 4 shows a perspective view of a vessel body of a bioreactor in isolation.
FIG. 5 shows a perspective view of a device for the supply or discharge of medium in isolation.

FIG. 4 shows another perspective view of the vessel body 12 from FIGS. 1 to 3. As can be seen in FIG. 4, the plug-in apertures 40 are configured as cutouts in the upper side 18 which are arranged in a row along the first edge 13 of the vessel body 12, at a distance from one another. In the same way, a plurality of plug-in apertures 40' are configured as cutouts which are arranged in a row along the second edge 15 of the vessel body 12, at a distance from one another.

FIG. 5 shows a perspective view of another device 42, 42' for the supply or discharge of medium which is similar in its design to the first and the second device 14, 16 from FIGS. 1 to 3. Here again, the first aperture 44 is configured at the end of the tube section 41 projecting beyond the surface of the cover 43. The cover 43 is of flat design, and is placed on the base body 45 to provide releasable closure of same. In addition, the base body 45 comprises a plurality of cutouts through which the nozzles 47 can pass, and a sealant 48 in the form of a gel is provided here to seal the intervening space between the respective nozzle 47 and the cutout associated therewith. As can be seen in FIG. 5, the nozzle 47 comprises a first and a second nozzle section 47*a, b*, there being a narrowing section 49 configured in the transition from the first to the second nozzle section 47*b*.

Figure 6:
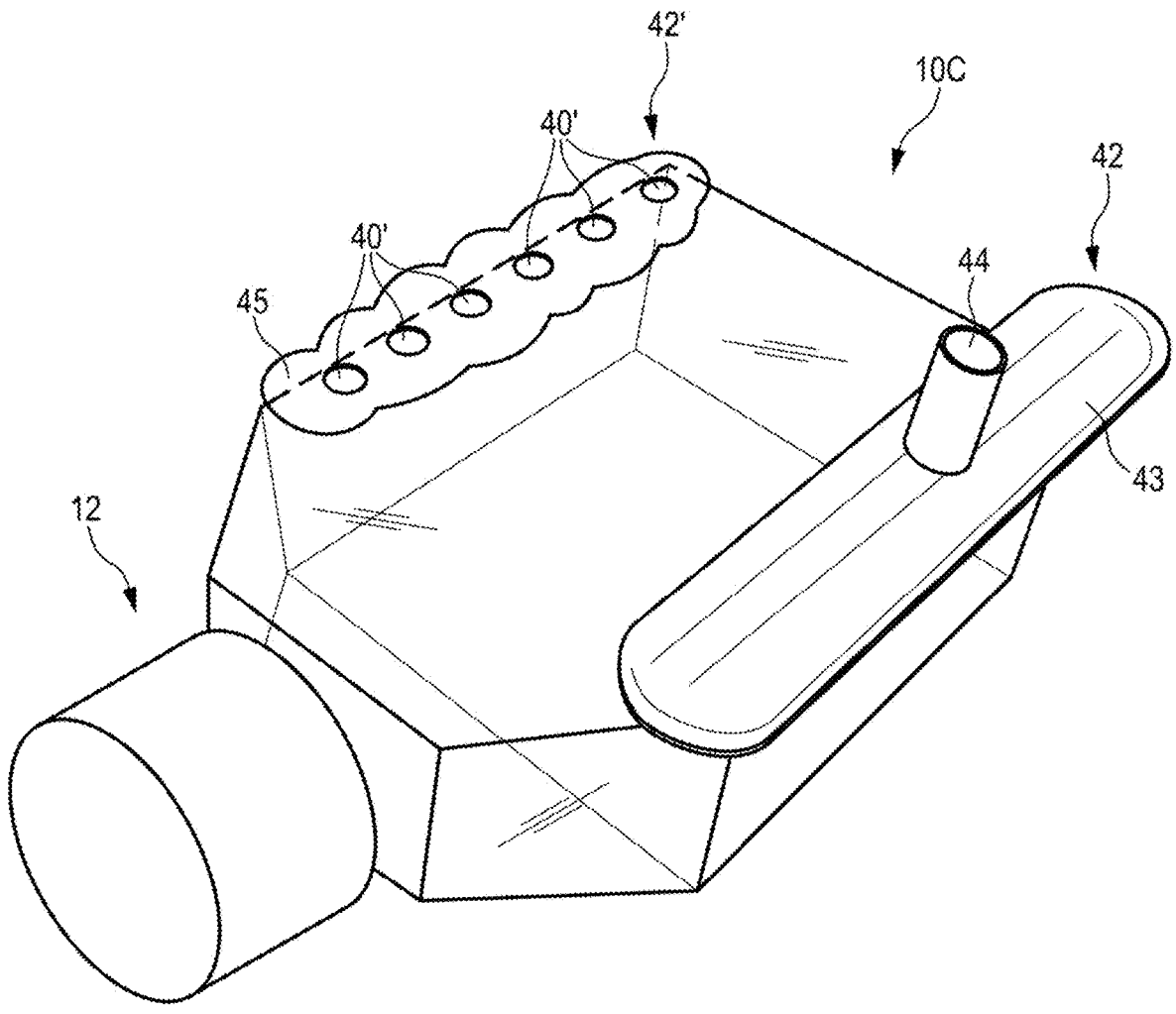
FIG. 6 shows another perspective view of the vessel body from FIG. 4, where the device from FIG. 5 is attached on the vessel body in order to form a bioreactor.

FIG. 6 shows a perspective view of another bioreactor 10C, which comprises the base body 45 from FIG. 4, and also two devices 42, 42' from FIG. 5. In one of the two devices 42, 42', the cover 43 is separated from the base body 45, and therefore only the base body 45 is attached on the vessel body 12. The bioreactor 100 is therefore in a partially built-up condition. The arrangement of the base body 45 is such that each of its plurality of cutouts respectively vertically overlaps a plug-in aperture 40' associated therewith of the vessel body 12. It is therefore possible, on closure of the base body 45 by the cover 43, to introduce the nozzles 47 of the device 42' through the cutouts and the plug-in apertures 40' into the vessel body 12.

The respective bioreactor 10A, B, C can be produced from glass and/or plastic. By way of example, the vessel body is produced primarily from glass, while the supply device, and the discharge device, is produced primarily from at least partially transparent plastic. The visibility of the medium flowing within the vessel body or through the supply device or discharge device is thus advantageously improved.

Figure 7:
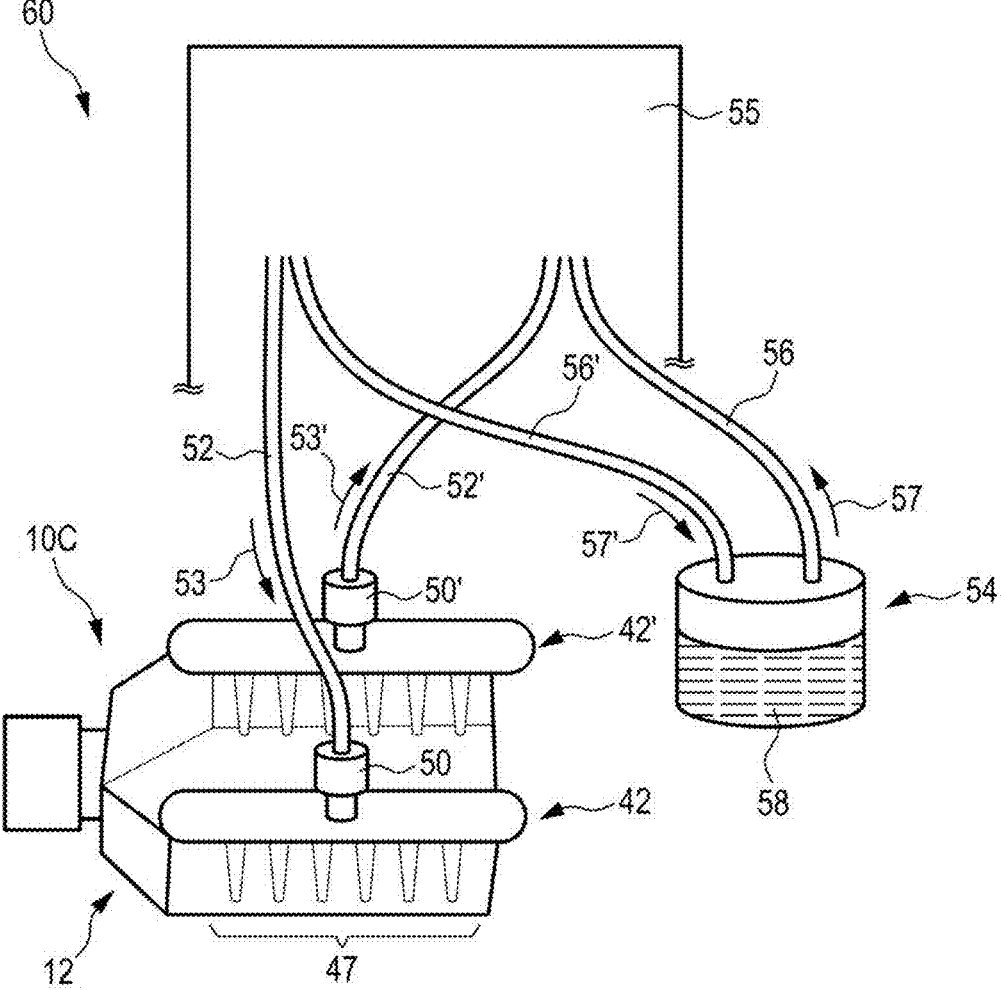
FIG. 7 shows a diagrammatic view of a system for the cultivation of microbiological systems, wherein the system comprises the bioreactor from FIG. 6, a medium reservoir and a pump, connected to one another by a plurality of flexible tubes.

Finally, FIG. 7 shows a greatly simplified diagrammatic depiction of a cultivation system 60. The cultivation system 60 comprises, alongside the bioreactor 100, a medium reservoir 54 and a pump 55, the various components here being connected to one another by way of a plurality of flexible tubes 52, 52' for the conduct of the medium through the system. A first flexible tube 56 between the medium reservoir 54 and the pump 55, and also a second flexible tube 52 between the pump 55 and the bioreactor 100, serve as input conduit, the directions of flow of the medium here being indicated by the arrows 53, 57. A third flexible tube 56' between the medium reservoir 54 and the pump 55, and also a fourth flexible tube 52' between the pump 55 and the bioreactor 100, serves as return conduit, the directions of the medium here being indicated by the arrows 53', 57'. It is also possible to use the bioreactor 10A or 10B instead of the bioreactor 100, the technical advantages thus achievable being the same. The flexible tubes 52, 52' are respectively connected by way of an adapter 50, 50' to the respective device 42, 42'.

The quantity of the medium 58 present in the vessel body 12 can be selected in a manner dependent on the shape and size of the vessel such that the medium 58 covers the cells located in the vessel body 12. The quantity present is preferably such that the level of the medium 58 is in the range of 0.001 mm to 20 mm above the bottom side 20. The flow rate of the medium is preferably in the range of 0.001 mL/min and 100 mL/min. With the aid of the devices 42, 42' it is possible to establish a flow configuration in which the supplied medium and the discharged medium has the same constant flow rate.

The cultivation system 60 shown in FIG. 7 is used to carry out laboratory experiments whose results are shown in FIG. 8A-D.

CnT-02 (obtainable by way of example from CELLnTEC advanced cell systems AG, Berne, Switzerland) supplemented+1 mM $CaCl_2$ is used as stratification medium for the conduct of experiments.

Urothelium cells from urethers are used as cell culture.

The cells are cultivated to confluence at 37° C. with 5% $CO_2$ in the bioreactor 100 shown in FIG. 7. During the duration of the experiment, the used-up medium is replaced by freshly constituted medium every two days. When confluence is complete, stratification of the cells is induced with the aid of the abovementioned stratifying medium. From that moment onward, the stratifying medium is replaced daily, the volume thereof present being 5 ml.

The flexible tubes 52, 52', and also the pump 55, are then attached to the bioreactor 100, the pump 55 here being adjusted to achieve and maintain a flow rate of 100 to 150 ml per hour.

Figures 8A, 8B, 8C, 8D:
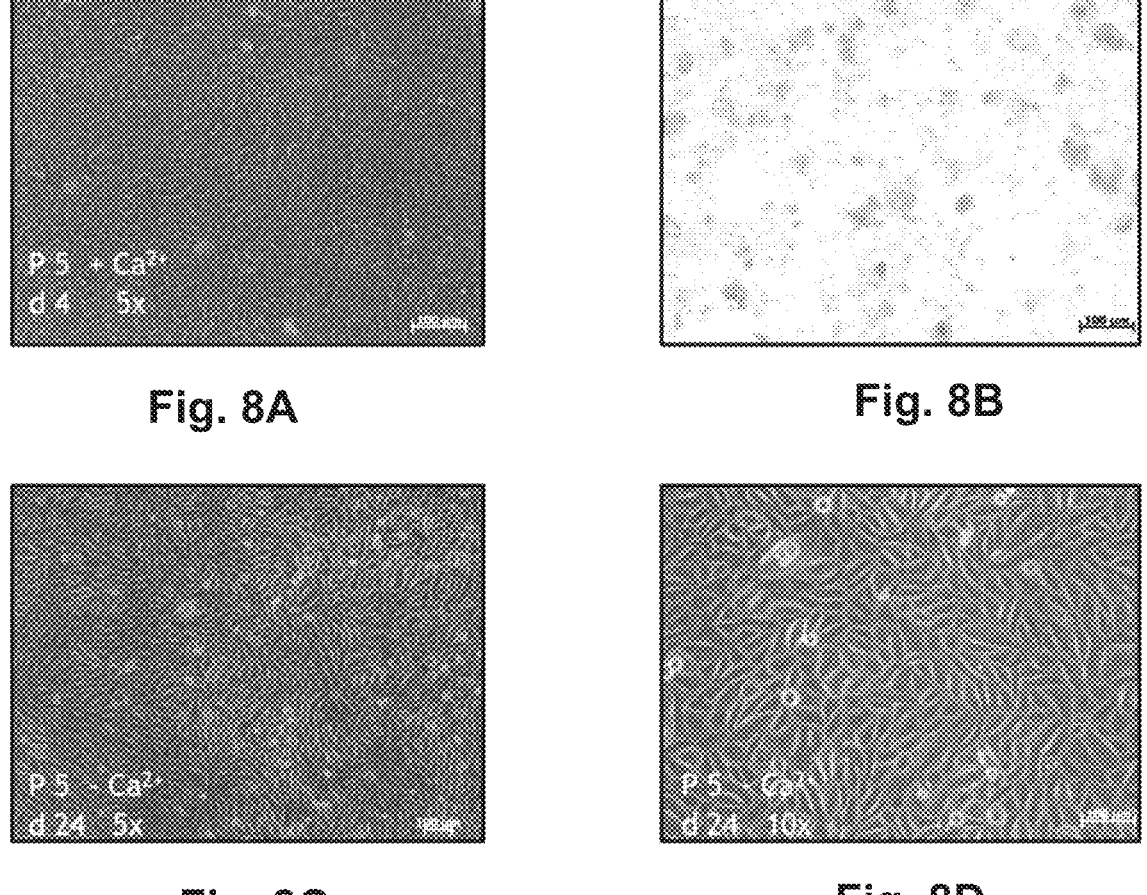
FIG. 8A-D shows microscope images of a cell culture obtained by means of the bioreactor from FIG. 7.

The stratification of the culture is maintained until the fourteenth day of the experiment. During the course of the experiment, a pellicle forms in the bioreactor 100; this separates from the bottom of the bioreactor 100 after a period of ten days. FIG. 8A shows a micrograph of the cell culture on the fourth day of the experiment (i.e. before separation of the pellicle) under 5× magnification. FIG. 8B shows another micrograph of the cell culture on the tenth day of the experiment (i.e. on the day on which the pellicle separated) under 10× magnification. FIG. 8C shows a micrograph of the cell culture on the twenty-fourth day of the experiment (i.e. after separation of the pellicle) under 5× magnification. FIG. 8D shows another micrograph of the cell structure from FIG. 8C under 10× magnification.

The separation of the multilayer cell pellicle is aided by a dispase (25 U/ml). As soon as the cell pellicle has separated from the bottom of the bioreactor 100, the dispase is removed by suction and 5 ml of PBS is pipetted into the system. The cell pellicle is transferred to a Petri dish and stored on ice.

The laboratory results show that in the bioreactor 100 it is possible to achieve appropriate cell propagation, which is progressed to confluence (FIG. 8A). Stratification in the experiment produces a urothelium in the form of a multilayer pellicle (FIGS. 8C and 8D). The bioreactor 100 can therefore be used to produce a biological tissue.

What is claimed is:

1. A culture vessel, comprising
a vessel body configured to accommodate a medium and extending from an upper side to a bottom side, and
at least one device configured to supply or discharge the medium into or out of the vessel body and arranged on the upper side of the vessel body, the at least one device comprising:
a housing,
a first aperture and a plurality of second apertures arranged on the housing,
the plurality of second apertures being connected with the first aperture in a fluid-conducting manner to supply the medium from the first aperture via the plurality of second apertures into an interior of the vessel body or to discharge the medium from the interior of the vessel body in a reversed direction, such that a plurality of medium sub-streams, arranged in parallel to one another, of the medium to be supplied or to be discharged are generated, wherein
the first aperture is connected with each of the plurality of second apertures respectively via one of a plurality of fluid conduits arranged in parallel to one another, wherein at least one of the plurality of fluid conduits is directed, at least in sections thereof, perpendicularly to the bottom side of the vessel body, and
wherein the plurality of fluid conduits are provided by a plurality of nozzles, wherein at least one of the plurality of nozzles is configured as a laminar nozzle for producing a laminar medium sub-stream of the medium that is to be supplied, wherein the laminar nozzle has a Reynolds number that is below 2300 for a flow velocity, and the medium has a viscosity sufficient for cell culture.

2. The culture vessel as claimed in claim 1, further comprising one or more plug-in apertures arranged on the upper side of the vessel body, wherein the plug-in apertures are configured to plug-in the at least one device.

3. The culture vessel as claimed in claim 1, wherein the at least one device comprises, on the vessel body, a first device for supply of the medium, and a second device for discharge of the medium.

4. The culture vessel as claimed in claim 3, wherein the first device and the second device are arranged at two mutually opposite edges of the vessel body.

5. The culture vessel as claimed in claim 1, wherein the vessel body comprises a connection for at least one of electrical current and voltage arranged for applying the at least one of electrical current and voltage on the vessel body.

6. The culture vessel as claimed in claim 1, configured as a bioreactor for cultivation of microbiological systems.

* * * * *